US012569515B2

(12) United States Patent　　(10) Patent No.: US 12,569,515 B2
Noe et al.　　(45) Date of Patent: Mar. 10, 2026

(54) GOLD-CONTAINING AGENTS FOR THE TREATMENT OF LUNG INFECTIONS

(71) Applicant: Aurovir Pharma GmbH, Vienna (AT)

(72) Inventors: Christian R. Noe, Vienna (AT); Marion Noe-Letschnig, Vienna (AT)

(73) Assignee: AUROVIR PHARMA GMBH, Vienna (AT)

( * ) Notice: Subject to any disclaimer, the term of this patent is extended or adjusted under 35 U.S.C. 154(b) by 525 days.

(21) Appl. No.: 17/906,241

(22) PCT Filed: Mar. 15, 2021

(86) PCT No.: PCT/EP2021/056554
§ 371 (c)(1),
(2) Date: Sep. 13, 2022

(87) PCT Pub. No.: WO2021/185773
PCT Pub. Date: Sep. 23, 2021

(65) Prior Publication Data
US 2023/0128434 A1　　Apr. 27, 2023

(30) Foreign Application Priority Data
Mar. 16, 2020　(AT) .............................. A 60074/2020

(51) Int. Cl.
| | |
|---|---|
| *A61K 33/242* | (2019.01) |
| *A61K 9/00* | (2006.01) |
| *A61K 31/198* | (2006.01) |
| *A61K 45/06* | (2006.01) |
| *A61K 47/10* | (2017.01) |
| *A61P 11/06* | (2006.01) |
| *A61P 31/04* | (2006.01) |
| *A61P 31/14* | (2006.01) |

(52) U.S. Cl.
CPC .......... *A61K 33/242* (2019.01); *A61K 9/0075* (2013.01); *A61K 9/0078* (2013.01); *A61K 31/198* (2013.01); *A61K 45/06* (2013.01); *A61K 47/10* (2013.01); *A61P 11/06* (2018.01); *A61P 31/14* (2018.01)

(58) Field of Classification Search
CPC .. A61K 33/242; A61K 9/0075; A61K 9/0078; A61K 31/198; A61K 47/26; A61K 2300/00; A61P 11/00; A61P 31/04
See application file for complete search history.

(56) References Cited

U.S. PATENT DOCUMENTS

| | | | | |
|---|---|---|---|---|
| 2011/0306935 A1* | 12/2011 | Tanaka | .................... | A61M 1/04 604/174 |
| 2017/0057993 A1* | 3/2017 | Wiles | .................... | C07D 401/12 |

FOREIGN PATENT DOCUMENTS

| | | |
|---|---|---|
| KR | 2015-0144679 A | 12/2015 |
| WO | 02/32418 A1 | 4/2002 |
| WO | 2012/142615 A2 | 10/2012 |
| WO | 2016/201524 A1 | 12/2016 |
| WO | 2017/058012 A1 | 1/2017 |
| WO | 2017/093544 A1 | 6/2017 |
| WO | 2021/011466 A1 | 1/2021 |

OTHER PUBLICATIONS

Millea, N-Acetylcysteine: Multiple clinical applications, American family physician, vol. 80, No. 3, pp. 265-269. (Year: 2009).*
European Patent Office, Communication Pursuant to Article 94(3) EPO, May 28, 2024.
Guido Domenighetti, et al., Treatment With N-Acetylcysteine During Acute Respiratory Distress Syndrome: A Randomized, Double-Blind, Placebo-Controlled Clinical Study, Journal of Critical Care, vol. 12, No. 4, 1997.
Kaushal Fowdar, M.D. er al., The effect of N-acetylcysteine on exacerbations of chronic obstructive pulmonary disease: A meta-analysis and systematic review, Heart and Lung Journal 46, 2017, pp. 120-128.
International Search Report for corresponding International Application No. PCT/EP2021/056554 mailed Jun. 22, 2021.
Written Opinion for corresponding International Application No. PCT/EP2021/056554 dated Jun. 22, 2021.
Rodriguez-Izquierdo et al., "Gold Nanoparticles Crossing Blood-Brain Barrier Prevent HSV-1 Infection and Reduce Herpes Associated Amyloid-ßsecretion", Journal of Clinical Medicine, 2020, 9, 155, doi:10.3390/jcm9010155 (cited in the specification).
Elkashif et al., "Investigation of auranofin and gold-containing analogues antibacterial activity against multidrug-resistant Neisseria gonorrhoeae", Scientific Reports, 2020, 10:5602 (https://doi.org/10.1038/s41598-020-62696-3), cited in the specification.
Bodas et al., "The NFKB Signaling in Cystic Fibrosis Lung Disease: Pathophysiology and Therapeutic Potential", National Institute of Health, Apr. 2010; 9(47): 346-356; cited in the specification.
Ori-Michael et al., "Gold Salts Therapy in Respiratory Diseases", Current Respiratory Medicine Reviews, 2013, 9, 328-333.
Britt et al., "The Thioredoxin Reductase-1 Inhibitor Aurothioglucose Attenuates Lung Injury and Improves Survival in a Murine Model of Acute Respiratory Distress Syndrome", Antioxidants & Redox Signaling, vol. 20, No. 17, 2014; DOI:10.1089/ars.2013/5332.
Colson et al., "Chloroquine and hydroxychloroquine as available weapons to fight COVID-19", International Journal of Antimicrobial Agents, 55, 2020, 105932.
Díez-Martínez et al., "Auranofin-loaded nanoparticles as a new therapeutic tools to fight streptococcal infections", Scientific Reports, Jan. 18, 2016, DOI:10.1038/srep19525.
Roopa Guthappa, "Molecular Docking Studies of N-Acetyl Cysteine, Zinc Acetyl Cysteine and Nisclosamide on SARS Cov2 Protease and Its Comparison with Hydroxychloroquine", ChemRxiv, Apr. 22, 2020, doi.org/10.26434/chemrxiv.12161493.vi.

(Continued)

*Primary Examiner* — Mina Haghighatian
(74) *Attorney, Agent, or Firm* — Chrisman Gallo Tochtrop LLC

(57) ABSTRACT

The present application relates to pharmaceuticals for inhalation, containing aurothioglucose, and to an inhaler, preferably a powder inhaler, dosing inhaler or atomizer containing such pharmaceuticals. The application provides these pharmaceuticals for use in the prevention and therapy of pulmonary diseases, in particular infectious and inflammatory-infectious pulmonary diseases.

21 Claims, 6 Drawing Sheets

(56) References Cited

OTHER PUBLICATIONS

Rothan et al., "The FDA-approved gold drug auranofin inhibits novel coronavirus (SARS-COV-2) replication and attenuates inflammation in human cells", Virology 547, 2020, 7-11.

Abdel Khalek et al., "Antibacterial and antivirulence activities of auranofin against Clostridium difficile", HHS Public Access, Int J Antimicrob Agents, Jan. 2019, 53(1), 54-62 doi:10.1016/j-ijantimicag. 2018.09.018.

Office Action dated Feb. 11, 2021 for corresponding Austrian Application No. A 60074/2020.

Broer et al., "Important Role for the Transmembrane Domain of Severe Acute Respiratory Syndrome Coronovirus Spike Protein during Entry", Journal of Virology, Feb. 2006, p. 1302-13-10; doi:10.1128/JVI.80.3.1302-1310.2006.

Chang et al., "Coronavirus-induced Membrane Fusion Requires the Cysteine-Rich Domain in the Spike Protein", Virology, 269, 212-224, 2000.

Gil-Moles et al., "Gold Metallodrugs to Target Coronavirus Proteins: Inhibitory Effects on the Spike-ACE2 Interaction and on PLpro Protease Activity by Auranofin and Gold Organometallics", Chemistry—A European Journal, doi.org/10.1002/chem. 202004112.

Kawayama et al., "Inhalation Therapy for Bronchial Asthma and COPD", The Journal of the Japan Society for Respiratory Care and Rehabilitation, 2014, vol. 24, No. 1, pp. 57-61.

Japanese Office action in corresponding application 2022-556110, dated Mar. 5, 2025.

Britt et al., "The Thioredoxin Reductase-1 Inhibitor Aurothioglucose Attenuates Lung Injury and Improves Survival in a Murine Model of Acute Respiratory Distress Syndrome", Therapeutics, Antioxidants & Redox Signaling, vol. 20, No. 17, 2014.

Huang et al., "N-acetylcysteine tiherapeutically protects against pulmonary fibrosis in a mouse model of silicosis", Portland Press, Bioscience Reports, 2019.

Kiso et al., "T-705 (favipiravir) activity against lethal H5N1 influenza A viruses", PNAS, vol. 107, No. 2, Jan. 12, 2010.

Li et al., "Attenuation of antimalarial agent hydroxychloroquine on TNF-$\alpha$-induced endothelial inflammation", International Immunopharmacology, 261-269, 2018.

* cited by examiner

Healthy

Placebo

Dexa-
methasone

AuAAC

Healthy

Placebo

Dexa-
methasone

AuAAC

—— Eosinophils

GOLD-CONTAINING AGENTS FOR THE TREATMENT OF LUNG INFECTIONS

CROSS-REFERENCE TO RELATED APPLICATIONS

This is a National Stage application of PCT international application PCT/EP2021/056554 filed on Mar. 15, 2021, which claims the priority of Austrian Patent Application No. A 60074/2020, filed Mar. 16, 2020, which are incorporated herein by reference in their entireties.

FIELD OF THE INVENTION

The present invention relates to the field of medicaments for the treatment of lung diseases, preferably infectious and mixed inflammatory and infectious lung diseases.

BACKGROUND OF THE INVENTION

Infectious lung diseases are widespread and constitute a huge social problem. On the one hand, as seasonal infections such as influenza, they are among the most common diseases, and on the other hand they are often the direct cause of death in affected people. The options for therapies in viral and/or bacterial infections of the respiratory tract have hitherto been insufficient.

Among infectious lung diseases, diseases which are caused by Coronaviridae have gained importance in recent years. SARS (Severe Acute Respiratory Syndrome) was first observed in November 2002 in the southern Chinese province of Guangdong. The pathogen for SARS was a coronavirus which was unknown until then and which has since been designated as "SARS-coronavirus (SARS-CoV-1) In 2019, the SARS-CoV-2 virus was discovered for the first time; it causes the disease Covid-19 and led to a global pandemic in 2020. MERS (Middle East Respiratory Syndrome) is also a lung disease which is caused by a coronavirus (MERS-CoV) and can sometimes lead to severe infection. A particularity of infections by SARS-CoV-2 compared with other viral infections is that entry to the cell is via the spike protein of the virus. The target of the spike protein is the membrane protein ACE2 (Angiotensin-2 Converting Enzyme), which plays an important role in the renin-angiotensin system, in that it cleaves the blood pressure-increasing angiotensin-2 enzymatically and therefore becomes its direct antagonist in physiological events. ACE inhibitors and AT2 antagonists are particularly important life-extending classes of medicaments for the treatment of high blood pressure and for the prevention of strokes and cardiac infarctions. They work in the same direction as physiological ACE2. In this way, every infection with SARS-CoV-2 also signifies a dysfunction in the function of one of the most important physiological systems.

In the case of severe COVID infections (or SARS-CoV-2 infections), the immune system reacts by overshooting, which becomes the actual cause of death. Thus, in the case of such infections, it is not helpful to restrict treatment to the viral infection alone, but rather, the dysfunction in the physiological system, above all in the immune system, should be treated at the same time.

Until now, there have been no sufficiently effective treatment methods to counter infections with coronaviruses, in particular SARS-CoV-1, SARS-CoV-2 and MERS. The nucleoside analogue remdesivir is sometimes used in SARS-CoV-2 as an antiviral treatment. Other therapeutic approaches are orientated towards the overshooting reaction of the immune system, for example by means of the steroid dexamethasone.

There is therefore a great need for novel therapies in lung diseases, in particular infectious and mixed inflammatory and infectious lung diseases. An objective of the invention is to provide such therapies.

Thus, the present invention provides medicaments for inhalation which contain gold, preferably aurothioglucose.

Pharmaceutical agents that contain gold are traditionally used in basic antirheumatic therapies. In recent years, the use of the most frequently employed pharmaceutical agents auranofin, aurothiomalate and aurothioglucose has been pushed back more and more often by the development of biologicals and the frequent occurrence of unwanted side effects during long term therapy, despite the fact that they are effective. Gold compounds are known to have a strong inflammation-inhibiting action, this being due to inhibition of the nuclear factor Nfkappa B. This factor also plays a central role in cystic fibrosis and in interstitial pneumonia which, inter alia, is a worrying consequence of viral lung infections.

At the same time, auranofin is known to have a considerable antibacterial and antibiofilm action (Abdel Khaleka et al, 2019). In addition, aurothioglucose has an antimicrobial activity (Elkashif and Seleem, 2020). An antiviral action has been described for gold nanoparticles (Rodriguez-Isqierdo et al., 2020). The antibacterial effectiveness has not as yet been the subject of licensed medicaments.

WO 2017/093544 A1 describes alkynylphosphine-gold complexes for the treatment of bacterial infections. WO 2017/058012 A1 discloses gold (III)-compounds for the treatment of COPD and asthma. WO 2012/142615 A2 describes auranofin and auranofin analogues for the treatment of proliferative diseases. WO 2021/011466 A1 describes metal nanoparticle compounds for the treatment of respiratory tract infections which are associated with cystic fibrosis. KR 2015/0144679 A discloses compositions for the prevention and treatment of immune diseases containing mesenchymal stem cells treated with a STAT3 inhibitor. WO 2016/201524 A1 discloses methods for the production of metal ion complexes in which the metal in particulate form is brought into contact with a chelating agent and a metallic complex is formed with the aid of an oxidizing agent.

The antimicrobial action of gold and gold compounds can be directly attributed to effects of gold ions on the microorganism. Both the noble metal gold as well as gold ions are highly unreactive. Apart from the ionic effects of gold ions, an exception to this is the high affinity of gold ions for sulphur atoms. Cysteine is a particularly important amino acid from a structural-functional viewpoint because it contributes substantially to the tertiary structure of proteins because of the possibility of forming disulphide bridges. Cysteine-rich domains are therefore very often located in the reactive centres of proteins.

Although the significance of pharmacokinetics has been known for a long time, particularly in the case of lung diseases, the fact that the direct topical application of a medicament to the site of the manifestation of the disease offers a wide range of important advantages such as, for example, the possibility of a lower dose, a lower physiological load and fewer side effects, is still being overlooked. Thus, gold-containing medicaments which are administered systemically can become stuck on sulphur atoms in amino acids and proteins on their way to the site of action. In the case of parenteral or oral administration, this may lead to accumulations in the body. Because of the side effects as a result of the strong interactions of the gold ions with sulphur compounds, the unfavourable pharmacokinetics with the usual oral and parenteral administration is a particularly major disadvantage of gold medication. Thus, the oral and parenteral forms of administration which have been normal until now are not very suitable for the treatment of lung infections with gold compounds. Injected or oral gold compounds have to be administered over long periods until the gold reaches the point of action in the lungs in an appropriate concentration. A pathway from introduction of the medicament into the body until the point of action which is as direct as possible could be seen in topical application. In addition, lung tissue is very good at taking up pharmaceuticals.

Our research has shown that aurothioglucose has a high affinity for the spike protein of SARS-CoV-2 virus. This too has a cysteine-rich domain to which the virus binds so strongly that ACE2, the natural attack point for the virus, can be efficiently pushed out of the bond. Because the spike protein-ace2 interaction is decisive for the attack of the virus on cells of the body, this discovery means that the antiviral action of gold compounds additionally also resides in a specific inhibition of the infection before the virus enters the cells of the body. This means that these compounds are also suitable for use in medicaments for the prevention of an infection. The anti-infective property contributes to the further antimicrobial and immunomodulatory properties and turns gold medications in inhalative application into unique medicaments for the topical treatment of spike protein-associated infections, especially SARS-CoV-2 infections. Because of their special properties, the medicaments in accordance with the invention are also particularly suitable for the prevention of viral infections.

BRIEF SUMMARY OF THE INVENTION

The present invention therefore concerns a medicament for inhalation which has a dual action—both against infection and against inflammation-immunomodulation, preferably a medicament which contains a gold-containing pharmaceutical agent such as aurothioglucose, aurothiomalate, auranofin, aurothiosulphate, aurotioprol and aurothiopolypeptide, or the gold salt of a sulphur-containing pharmaceutical agent such as acetylcysteine, pyritinol, tiopronin and penicillamine.

The gold salt of N-acetylcysteine is a particularly preferred compound from among the gold salts of pharmaceutical agents, because N-acetylcysteine is already used in the treatment of lung diseases as the pharmaceutical agent acetylcysteine and a positive additional therapeutic effect can be expected.

Although the pivotal point is the action of the medicaments of the invention on the gold ion, the counter-ion is also of major significance. Thus, the toxic phosphine part of auranofin considerably restricts its dosage options. In addition, the release of the gold ion from the compound is to a large extent determined by the counter-ion.

The respective therapeutic relevance of the anti-infective or anti-inflammatory-immunomodulatory action is time-dependent. While infection inhibition and propagation in the early phase of the disease are of very particular importance, in the late phases and above all in severe infections, immunomodulation becomes particularly important. In aurothioglucose and aurothiomalate, binding of the gold ion to the spike protein can be significantly improved by means of a further compound which contains a mercapto group, whereupon it is possible to control the activity profile of the medicament in a manner such that either the anti-infective profile prior to resorption (upon activation) or the anti-inflammatory-immunomodulatory profile after resorption (without activation) is in the foreground. In this manner, when using these compounds without the activating addition, the anti-inflammatory-immunomodulatory effect is in the foreground. Preferred pharmaceutical agents in severe infections are therefore aurothioglucose and aurothiomalate, particularly preferably aurothioglucose.

In respect of the compounds which contain mercapto groups, it has been shown that the addition of N-acetylcysteine results in an increase in efficacy (see Example 6, for example). A combination of aurothioglucose and aurothiomalate with N-acetylcysteine has been shown to be particularly advantageous. Thus, in a further aspect, the invention provides a combination medicament in which the gold-containing compound is combined with a compound which contains a mercapto group, preferably with N-acetylcysteine.

In antiviral therapies, the use of combinations of pharmaceutical agents has proved to be advantageous; they attack different targets and in this manner, both increase the anti-infective action and also inhibit the development of resistance by mutation. The anti-infective action of gold compounds is based on different targets. Thus, during the course of the investigations in respect of the present patent application, a high affinity for the papain-like protease PLpro as well as for the chymotrypsin-like protease 3CLpro was found. Both proteases are essential for virus proliferation and represent important target structures for the development of antiviral pharmaceutical agents against SARS-CoV-2 and other viruses. By adding antiviral pharmaceutical agents, preferably those which attack virus RNA synthesis, a further enhancement of the antiviral effect can be expected.

In one aspect, the invention concerns a medicament for inhalation, containing gold, preferably aurothioglucose, aurothiomalate, auranofin, aurothiosulphate, aurotioprol, aurothiopolypeptide and/or the gold salt of a sulphur-containing pharmaceutical agent (preferably N-acetylcysteine, pyritinol, tiopronin and/or penicillamine), in particular aurothioglucose.

In a preferred embodiment, the medicament further contains N-acetylcysteine.

More preferably, the medicament contains a further active substance, preferably wherein the further active substance has an antiviral and/or antibacterial action. In a preferred embodiment, the medicament contains a virostatic, preferably selected from the group consisting of remdesivir, molnupiravir, favipiravir, ribavirin, lopinavir, umifenovir, nelfinavir and/or ritonavir, preferably favipiravir, molnupiravir and/or ribavirin, in particular favipiravir. A combination of aurothioglucose and aurothiomalate with one of the preferred virostatics has been shown to be particularly advantageous. In a preferred embodiment, the medicament containing the virostatic additionally contains N-acetylcysteine (for example as a triple combination containing gold, in particular, aurothioglucose, N-acetylcysteine and a virostatic, in particular the combination of aurothioglucose+N-acetylcysteine+favipiravir or the combination aurothioglucose+N-acetylcysteine+molnupiravir).

In a further preferred embodiment, the medicament contains an active substance selected from hydroxychloroquine, chloroquine and/or ivermectin. Preferably, the medicament additionally contains N-acetylcysteine (for example as a triple combination containing gold, in particular aurothioglucose, N-acetylcysteine and an active substance selected from hydroxychloroquine, chloroquine and/or ivermectin). In a further preferred embodiment, the medicament (with or without N-acetylcysteine) additionally contains a virostatic as described herein.

In a further aspect, the invention provides an inhaler, preferably a powder inhaler, dosing inhaler or nebulizer, containing a medicament in accordance with the invention.

In a further aspect, the invention provides the medicament in accordance with the invention for use in the prevention or treatment of lung diseases, preferably in the prevention or treatment of inflammatory, infectious and mixed inflammatory and infectious lung diseases, in particular SARS (Severe Acute Respiratory Syndrome), MERS (Middle East Respiratory Syndrome), or Covid-19.

By means of the present invention, gold-containing agents for therapy and their use for the treatment of infectious and mixed inflammatory and infectious lung diseases are provided, in which the active substance advantageously gains direct access to the site of action in the lungs by inhalation and can act there. By means of this mode of application, at the same time, side effects are reduced to the smallest possible measure.

Microbial infections are usually associated with inflammatory processes. This finding is not a random coincidence, but is made necessary by synchronous pathogen-host interactions. It has therefore been shown that in order to treat microbial infections, active substances with a dual anti-infective and anti-inflammatory action are particularly suitable. The dual action of the gold compounds in this regard can offer a particular advantage, because the inflammation-inhibiting action occurs by inhibiting the nuclear factor NFkappa B (Bodas M. and Vij N, 2010) which, inter alia, contributes to the occurrence of interstitial pneumonia. The anti-inflammatory action of the agents in accordance with the invention is comparable with that of inhalative steroids (see Example 3, for example).

Gold-containing agents in accordance with the invention for the treatment of diseases which are caused by Coronaviridae from the RNA virus group such as SARS (Severe Acute Respiratory Syndrome) MERS-CoV (Middle East Respiratory Syndrome Coronavirus) and SARS-CoV-2, are particularly preferred. The gold-containing agents in accordance with the invention bind with a high affinity to cysteine mercapto group-rich domains of binding proteins of these viruses, in particular coronaviruses, which is functionally essential for binding thereof to the host cells and for fusion (Chang et al, 2000, Broer et al., 2006). In addition, these viral diseases are often accompanied by bacterial super-infections with biofilm formation, against which the agents in accordance with the invention are also active. Auranofin and other gold complexes inhibit the interaction of the spike protein of SARS-CoV-2 with the ACE2 receptor (ACE2: Angiotensin Converting Enzyme 2). Furthermore, gold complexes inhibit the activity of the viral protease PLpro (PLpro: Papain-Like Protease) of SARS-CoV-1 and SARS-CoV-2. Auranofin has $IC_{50}$ values of 22.2 mM against the spike/ACE2-interaction and 0.75 mM against PLpro from SARS-CoV-2 (Gil-Moles et al., 2020).

The preferred form of administration of the agent is inhalation as a liquid aerosol or by powder inhalation. The latter is distinguished from the former by the easier to handle liquid inhalation, during which considerable quantities of the active substance remain in the pharyngeal cavity, by a more precise opportunity for dosing. Elemental gold can be used in the form of nanoparticles; however, the pharmaceutical agents aurothioglucose, aurothiomalate and auranofin and the salt auroacetylcysteine, in which the gold is in the ionic form, which have been proven effective in antirheumatics practice, are preferred. Aurothioglucose has the advantage that the gold ion is particularly strongly bonded to the molecule and therefore can be released in a more controlled manner.

For the purposes of inhalation, commercially available devices may be used. In the case of intensive medical treatments, aqueous solutions of the agents in accordance with the invention may be added to ventilation air using spray nozzles. In the case of powder inhalation, micronization of the active substance (particle size preferably less than 5 micrometres) is a preferred form of administration, because in this manner, deeper areas of the lungs are reached. In addition, use as a mixture with a support material is preferred. In this regard, mixing the micronized active substance with a support material with a larger grain size is particularly preferred, because this guarantees that firstly, the support material is deposited in the upper regions of the pharyngeal cavity and more of the active substance penetrates into the lower areas of the lungs. Lactose, mannose and other carbohydrates are suitable support materials.

In respect of combination medicaments, the active substances are preferably placed in separate compartments of a powder inhaler. Placing the active substances in separate compartments facilitates manufacture, inter alia. In a preferred embodiment of the powder inhaler, therefore, gold or aurothioglucose and N-acetylcysteine are in separate compartments of the powder inhaler. In a particularly preferred embodiment of the powder inhaler, gold or aurothioglucose and the virostatic are in separate compartments of the powder inhaler. In the case of the triple combination described herein, all three active substances may be present in separate compartments of the powder inhaler.

In the context of the invention, the medicament for use in accordance with the invention preferably contains a gold-containing antirheumatic pharmaceutical agent. Particularly preferred antirheumatic pharmaceutical agents are aurothioglucose, aurothiomalate, auranofin, aurothiosulphate, aurotioprol and/or aurothiopolypeptide. Aurothioglucose in particular has been shown to be particularly advantageous in the context of the invention.

Preferably, the medicament contains auxiliary substances. Particularly preferred auxiliary substances are those which are in normal use in formulations for inhalation, in particular powder and liquid formulations for inhalation. In a preferred embodiment, the medicament contains a support material, preferably a carbohydrate, particularly preferably lactose and/or mannose.

In a preferred embodiment, the medicament contains a further active substance for use; preferably, the further active substance has an antiviral and/or antibacterial action. Virostatics, in particular favipiravir, molnupiravir, remdesivir or ribavirin, are particularly preferred.

In the context of the invention, the lung disease is preferably a lung infection, preferably a viral or mixed viral and bacterial lung infection, more preferably a disease which is caused by Coronaviridae belonging to the RNA virus group, in particular SARS-CoV-1, SARS-CoV-2 or MERS-CoV. In this regard, it is preferably a coronavirus infection, in particular a SARS-CoV-1 infection, a SARS-CoV-2 infection or a MERS-CoV infection. Particularly preferably, the lung disease is SARS (triggered by a SARS-CoV-1 infection), Covid-19 (triggered by a SARS-CoV-2 infection), or MERS (triggered by a MERS-CoV infection).

In respect of all of the aspects of the invention, the medicament is preferably used by inhalation. Liquid inhalation or powder inhalation is particularly preferred. More particularly preferably, the administration is carried out by means of an inhaler in accordance with the invention.

In a preferred embodiment, the dual-action medicament of the invention contains gold (preferably in the form of aurothioglucose, aurothiomalate, auranofin, aurothiosulphate, aurotioprol, and/or aurothiopolypeptide and no other active substances.

In a further preferred embodiment, the medicament in accordance with the invention contains gold (preferably in the form of aurothioglucose, aurothiomalate, auranofin, aurothiosulphate, aurotioprol, and/or aurothiopolypeptide, in particular aurothioglucose) and N-acetylcysteine in a molar ratio of between 1:40 and 10:1, preferably between 1:20 and 5:1, more preferably between 1:10 and 2.5:1, yet more preferably between 1:5 and 1:1, yet more preferably between 1:2.5 and 1:1.5, most preferably 1:2 (gold:N-acetylcysteine).

In respect of all of the medicaments in accordance with the invention, the medicament is preferably presented as a formulation for inhalation. Particularly preferably, the formulation is a powder formulation. Preferably, the medicament is presented as a dry powder for aerosol preparation. A powder formulation means that a particularly simple administration is possible, for example by means of a powder inhaler. As an example, powder inhalers like those already used for the treatment of asthma or COPD may be used. For this application, the medicament is preferably micronized.

In a further preferred embodiment, the medicament is presented as a powder or solution for aerosol preparation. This formulation is particularly suitable for administration by dosing inhalers or nebulizers. As an example, such formulations may also be used for patients who have to be artificially ventilated, for example in severe cases of coronavirus infections, in particular SARS, Covid-19 or MERS.

In a preferred embodiment, the inhaler in accordance with the invention is a powder inhaler, wherein the medicament in accordance with the invention is presented as a powder formulation. In a further preferred embodiment, the inhaler is a dosing inhaler (for example a pressurized gas dosing inhaler or a normal pressure dosing inhaler) or nebulizer, wherein the medicament is presented as a solution or as an aerosol.

Furthermore, the invention discloses a method for the prevention or treatment of a lung disease, preferably of an infectious or mixed inflammatory and infectious lung disease, comprising the steps of:
    providing a medicament or a combination medicament as described herein; and
    administering an effective quantity of the medicament or of the combination medicament to an individual who requires it. Preferably, the method is for the treatment of the lung disease, wherein the individual suffers from the lung disease.

All of the preferred embodiments for the medicament for application in accordance with the invention are also preferred for the treatment method disclosed herein. In particular, all of the preferred embodiments of the lung disease are also preferred for this method. Preferably, the administration of the medicament is carried out by means of an inhaler in accordance with the invention.

The term "prevention" as used herein means completely or almost completely or at least to a (preferably significant) extent preventing the occurrence of a disease in an individual. However, this term should not be interpreted as complete success in the sense that the individual can never develop such a disease, but in the sense of reducing the risk of disease.

In the context of the present invention, the terms "agent", "pharmaceutical" or "pharmaceutical composition" should be understood to mean a composition containing at least one active substance and preferably containing one or more pharmaceutically acceptable auxiliary substances. In particular, these compositions are for administration to an animal, preferably to a mammal, and most preferably to a human being.

Preferably, a dose of the medicament is administered to an individual, wherein preferably, a dose of the medicament is administered at least once per week, preferably at least every two days, more preferably at least once a day, yet more preferably at least twice per day, in particular at least three times per day.

Preferably, the therapy is carried out over a specific period of time and with an effective quantity of medicament. In particular, the medicament is preferably administered over a time period of 1 to 30 days, preferably 2 to 21 days, more preferably 3 to 14 days, and most preferably 5 to 10 days.

In the context of the present invention, the individual to be treated is preferably an animal, preferably a mammal, in particular a human being. Preferably, the individual has one of the lung diseases described herein.

In a preferred embodiment, the concentration of gold in a dose of the medicament is between 0.001 μmol and 450 μmol, preferably between 0.01 μmol and 250 μmol, yet more preferably between 0.1 μmol and 50 μmol, most preferably between 0.5 μmol and 30 μmol. In a particularly preferred embodiment, a dose contains between 0.1 μg and 1000 μg of gold per kg body weight of the patient, preferably between 0.2 μg/kg and 200 μg/kg, more preferably between 0.5 μg/kg and 40 μg/kg, most preferably between 1 μg/kg and 10 μg/kg body weight.

In particular, the present invention discloses the following preferred embodiments:

Embodiment A1. Medicament for inhalation containing gold, preferably aurothioglucose, aurothiomalate, auranofin, aurothiosulphate, aurotioprol, aurothiopolypeptide, and/or the gold salt of a sulphur-containing pharmaceutical agent (preferably N-acetylcysteine, pyritinol, tiopronin and/or penicillamine), in particular aurothioglucose.

Embodiment A2. Medicament in accordance with embodiment A1, characterized in that the medicament contains a gold-containing antirheumatic pharmaceutical agent, preferably aurothioglucose, aurothiomalate, auranofin, aurothiosulphate, aurotioprol, and/or aurothiopolypeptide, in particular aurothioglucose.

Embodiment A3. Medicament for inhalation, containing aurothioglucose.

Embodiment A4. Medicament in accordance with one of embodiments A1 to A3, further containing N-acetylcysteine.

Embodiment A5. Medicament in accordance with one of embodiments A1 to A4, characterized in that the medicament contains a further active substance, preferably wherein the further active substance has an antiviral and/or antibacterial action.

Embodiment A6. Medicament in accordance with one of embodiments A1 to A5, further containing a virostatic, preferably selected from the group consisting of remdesivir, molnupiravir, favipiravir, ribavirin, lopinavir, umifenovir, nelfinavir and/or ritonavir, preferably favipiravir, molnupiravir and/or ribavirin, in particular favipiravir.

Embodiment A7. Medicament in accordance with one of embodiments A1 to A6, further containing an active substance selected from hydroxychloroquine, chloroquine and/or ivermectin.

Embodiment A8. Medicament for inhalation containing gold, preferably aurothioglucose, aurothiomalate, auranofin, aurothiosulphate, aurotioprol, aurothiopolypeptide, and/or the gold salt of a sulphur-containing pharmaceutical agent (preferably N-acetylcysteine, pyritinol, tiopronin and/or penicillamine), in particular aurothioglucose;

a virostatic, preferably selected from the group consisting of remdesivir, molnupiravir, favipiravir, ribavirin, lopinavir, umifenovir, nelfinavir and/or ritonavir, preferably favipiravir, molnupiravir and/or ribavirin, in particular favipiravir; and N-acetylcysteine.

Embodiment A9. Medicament in accordance with one of embodiments A1 to A8, characterized in that the medicament contains gold and N-acetylcysteine in a molar ratio of between 1:40 and 10:1, preferably between 1:20 and 5:1, more preferably between 1:10 and 2.5:1, yet more preferably between 1:5 and 1:1, yet more preferably between 1:2.5 and 1:1.5, most preferably 1:2 (gold:N-acetylcysteine).

Embodiment A10. Medicament in accordance with one of embodiments A1 to A9, characterized in that the medicament contains aurothioglucose and N-acetylcysteine in a molar ratio of between 1:40 and 10:1, preferably between 1:20 and 5:1, more preferably between 1:10 and 2.5:1, yet more preferably between 1:5 and 1:1, yet more preferably between 1:2.5 and 1:1.5, most preferably 1:2 (aurothioglucose:N-acetylcysteine).

Embodiment A11. Medicament in accordance with one of embodiments A1 to A10, characterized in that the medicament contains a support material, preferably a carbohydrate, particularly preferably lactose and/or mannose.

Embodiment A12. Medicament in accordance with one of embodiments A1 to A11, characterized in that the medicament is presented as a powder formulation, preferably micronized.

Embodiment A13. Medicament in accordance with one of embodiments A1 to A11, characterized in that the medicament is presented as a solution or as an aerosol.

Embodiment A14. Inhaler, preferably powder inhaler, dosing inhaler or nebulizer, containing a medicament in accordance with one of embodiments A1 to A13.

Embodiment A15. Inhaler, preferably powder inhaler, containing a medicament in accordance with embodiment A12.

Embodiment A16. Inhaler, preferably dosing inhaler or nebulizer, containing a medicament in accordance with embodiment A13.

Embodiment A17. Powder inhaler containing a medicament in accordance with one of embodiments A4 to A12, characterized in that gold or aurothioglucose and N-acetylcysteine are presented in separate compartments of the powder inhaler.

Embodiment A18. Powder inhaler containing a medicament in accordance with one of embodiments A5 to A12, characterized in that gold or aurothioglucose and the further active substance are presented in separate compartments of the powder inhaler.

Embodiment A19. Powder inhaler containing a medicament in accordance with one of embodiments A6 to A12, characterized in that gold or aurothioglucose and the virostatic are presented in separate compartments of the powder inhaler.

Embodiment A20. Medicament in accordance with one of embodiments A1 to A13 for application in the prevention or treatment of lung diseases, preferably in the prevention or therapy of inflammatory, infectious and mixed inflammatory and infectious lung diseases.

Embodiment A21. Medicament for use in accordance with embodiment A20, characterized in that the lung disease is an infectious or mixed inflammatory and infectious lung disease.

Embodiment A22. Medicament for use in accordance with one of embodiments A20 or A21, characterized in that the lung disease is caused by a lung infection, preferably a viral or mixed viral and bacterial lung infection, more preferably a disease which is caused by Coronaviridae belonging to the RNA virus group, in particular SARS-CoV-1, SARS-CoV-2 or MERS-CoV.

Embodiment A23. Medicament for use in accordance with one of embodiments A20 to A22, characterized in that the lung disease is SARS, MERS or Covid-19.

Embodiment A24. Medicament for use in accordance with embodiment A20, characterized in that the lung disease is an inflammatory lung disease, preferably a chronic inflammatory lung disease, in particular COPD, cystic fibrosis or interstitial pneumonia.

Embodiment A25. Medicament for use in accordance with one of embodiments A20 to A24, characterized in that the medicament is administered in a dose containing between 0.001 μmol and 450 μmol, preferably between 0.01 μmol and 250 μmol, more preferably between 0.1 μmol and 50 μmol, most preferably between 0.5 μmol and 30 μmol of gold.

Embodiment A26. Medicament for use in accordance with one of embodiments A20 to A25, characterized in that the medicament is administered in a dose containing between 0.1 μg and 1000 μg of gold per kg of body weight of the patient, preferably between 0.2 μg/kg and 200 μg/kg, more preferably between 0.5 μg/kg and 40 μg/kg, most preferably between 1 μg/kg and 10 μg/kg of body weight of gold.

Embodiment A27. Medicament for use in accordance with one of embodiments A20 to A26, characterized in that the use is by means of inhalation, preferably liquid inhalation or powder inhalation.

Embodiment A28. Medicament for use in accordance with one of embodiments A20 to A27, characterized in that the use is by means of an inhaler in accordance with one of embodiments A14 to A19.

Embodiment A27. Method for the prevention or treatment of a lung disease, preferably a lung disease as defined in one of embodiments A20 to A26, comprising the steps of:

providing a medicament as defined in one of embodiments A1 to A13; and administering an effective quantity of the medicament to an individual who requires it.

Embodiment A28. Method in accordance with embodiment A27, wherein the method is as defined in one of the embodiments A20 to A26.

Embodiment A29. Method in accordance with embodiment A27 or A28, characterized in that the medicament is administered by means of an inhaler, preferably by means of an inhaler in accordance with one of embodiments A14 to A19.

Embodiment B1. Agents for the treatment of inflammatory, infectious and mixed inflammatory and infectious lung diseases, characterized in that they contain gold.

Embodiment B2. Agents in accordance with embodiment B1, characterized in that they are used for the inhalative treatment of lung infections.

Embodiment B3. Agents in accordance with embodiment B1, characterized in that they are used for the inhalative treatment of viral and mixed viral and bacterial lung infections.

Embodiment B4. Agent in accordance with embodiments B1-B3, characterized in that the gold-containing substance is either a pharmaceutical agent for the treatment of rheumatic diseases or the gold salt of a pharmaceutical agent or nanoparticulate gold.

Embodiment B5. Agent in accordance with embodiments B1-B4, characterized in that the antirheumatic pharmaceutical agent is aurothioglucose.

Embodiment B6. Agent in accordance with embodiments B1-B4, characterized in that the antirheumatic pharmaceutical agent is aurothiomalate.

Embodiment B7. Agent in accordance with embodiments B1-B4, characterized in that the antirheumatic pharmaceutical agent is auranofin.

Embodiment B8. Agent in accordance with embodiments B1-B4, characterized in that the active substance is the gold salt of an acidic pharmaceutical agent, preferably N-acetyl-cysteine.

Embodiment B9. Agent in accordance with embodiments B1-B8, characterized in that the application is carried out by liquid inhalation.

Embodiment B10. Agent in accordance with embodiments B1-B8, characterized in that the application is carried out by powder inhalation.

Embodiment B11. Agent in accordance with embodiment B10, characterized in that the pharmaceutical agent is diluted with a support material.

Embodiment B12. Agent in accordance with embodiment B10 and B11, characterized in that the support material is a carbohydrate, preferably lactose or mannose.

Embodiment B13. Agent in accordance with embodiment B10, characterized in that the pharmaceutical agent is used in a micronized form.

Embodiment B14. Medicament in accordance with embodiments B1-B13, characterized in that it contains at least one further active substance.

Embodiment B15. Agent in accordance with embodiment B14, characterized in that the additional active substance has an antiviral action.

Embodiment B16. Agent in accordance with embodiments B14 and B15, characterized in that the additional active substance has an antibacterial action.

Embodiment B17. The use of agents in accordance with embodiments B1-B16 for the treatment of infectious and mixed inflammatory infectious diseases of the respiratory tract.

Embodiment B18. The use of agents in accordance with embodiments B17 for the treatment of diseases caused by Coronaviridae belonging to the RNA virus group, such as SARS (Severe Acute Respiratory Syndrome), MERS-CoV (Middle East Respiratory Syndrome Corona Virus), SARS-CoV-2 and Covid-19.

Embodiment B19. The use of agents in accordance with embodiments B1-B16 for the treatment of inflammatory lung diseases, preferably chronic inflammations such as COPD, cystic fibrosis and interstitial pneumonia.

Embodiment B20. The use of auroacetylcysteine in medicaments in accordance with embodiments B17-B19.

BRIEF DESCRIPTION OF THE DRAWINGS

The present invention will now be illustrated with the aid of the following examples and figures; they are obviously not limited thereto.

DESCRIPTION OF EXAMPLE EMBODIMENTS

EXAMPLES

Example 1. Production of Single Doses for Inhalation 1.a. Liquid ampoule: A solution of 1.5 mg of auranofin in 2.5 mL sodium chloride-containing water was introduced into a single dose container and introduced into a nebulizer for use.

1.b. Dry ampoule: An ampoule was filled with 1.5 mg of aurothioglucose. Prior to use, 2.5 mL of water was injected and the solution was introduced into an inhaler. The prepared product had to be consumed within 3 hours.

Example 2. Production of Multiple Doses for Inhalation 2.a. Powder spray: 30 mg of micronized aurothioglucose was suspended in 300 microlitres of ethanol. 30 mg of sorbitan trioleate was added and then added to a spray bottle with 15 g of propellant, with cooling; there were 300 spray applications of the product.

2.b. Dry inhaler: 0.2 mg of micronized aurothioglucose was blended with 12 mg of lactose and prepared for powder inhalation with the strict exclusion of moisture. This was dependent on the type of inhaler and could, if necessary, involve compression into a disk.

Figure 1:
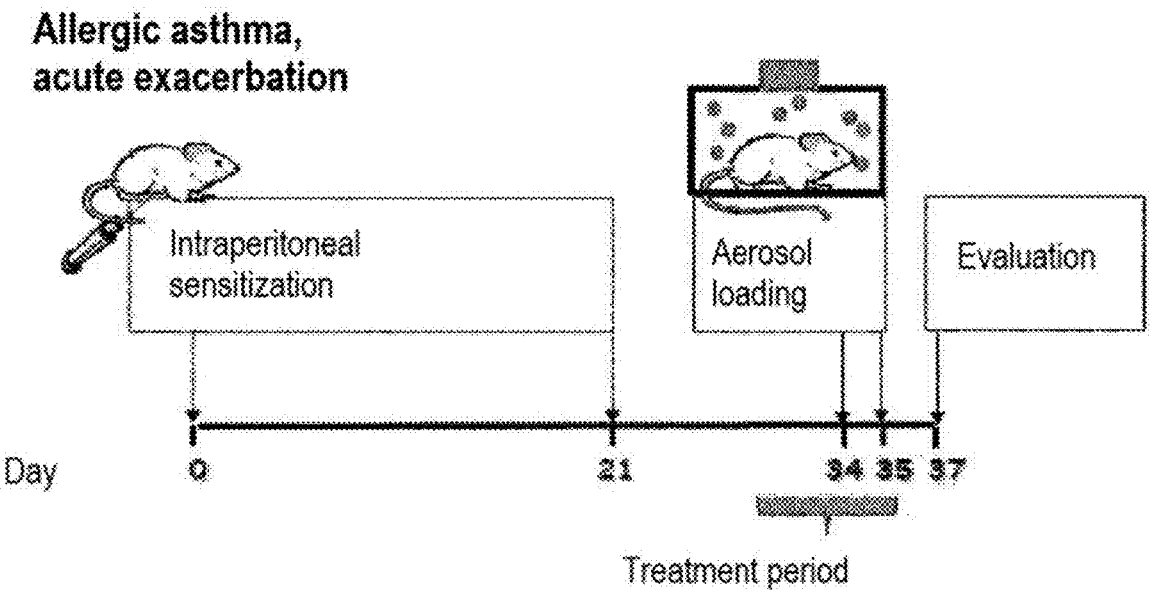
FIG. 1. Anti-inflammatory effectiveness of auroacetylcysteine in a mouse model for acute allergic asthma: experimental setup.
Figure 2:
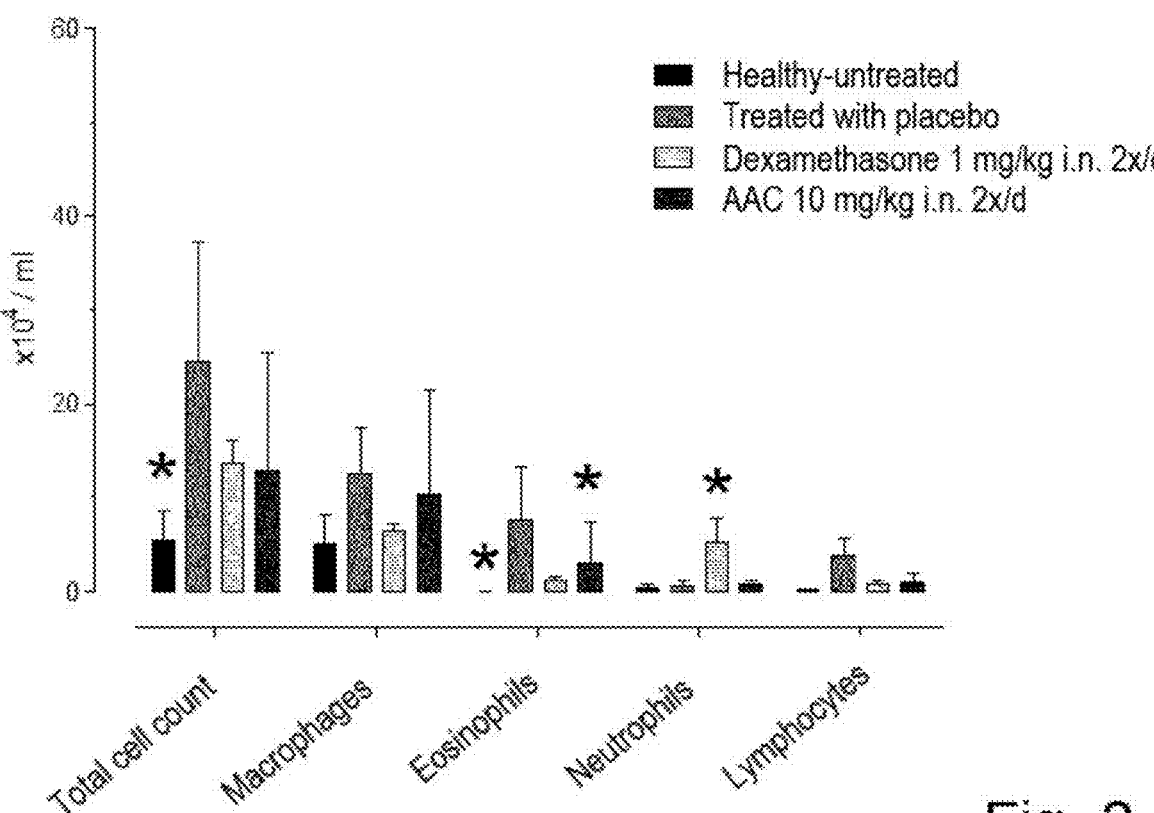
FIG. 2. Anti-inflammatory effectiveness of auroacetylcysteine in a mouse model for acute allergic asthma: cell count in bronchoalveolar lavage for the investigation of inflammation of the respiratory tract. Graph: mean±SD, n=5 except for AAC group (n=4 (because of one death) * P<0.05 compared with placebo (support material), Kruskal-Wallis Test, Dunn's multiple comparison test.
Figure 3:
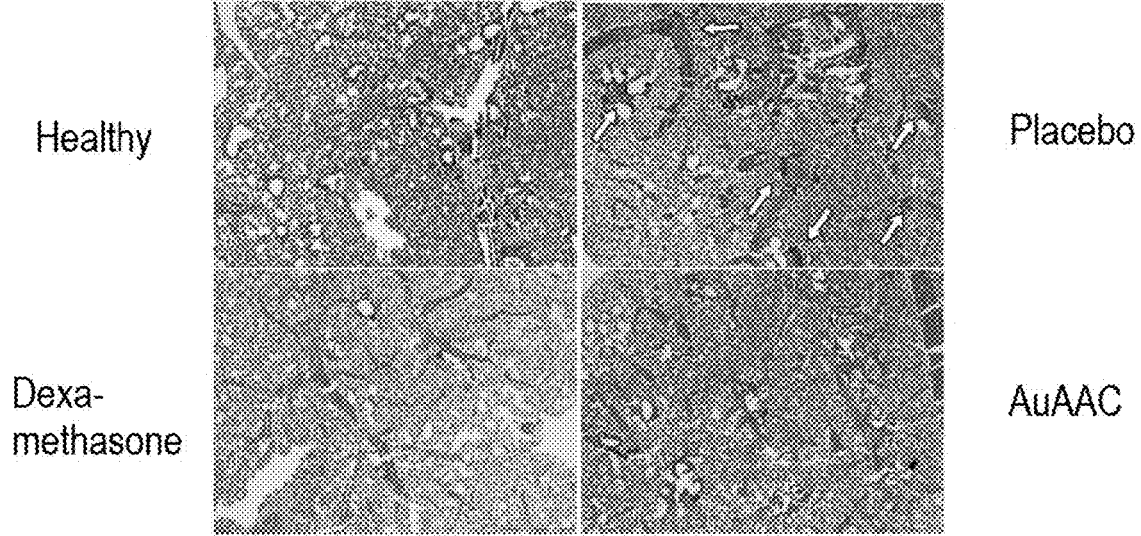
FIG. 3. Anti-inflammatory effectiveness of auroacetylcysteine in a mouse model for acute allergic asthma: histological investigation of lung tissue.
Figure 4:
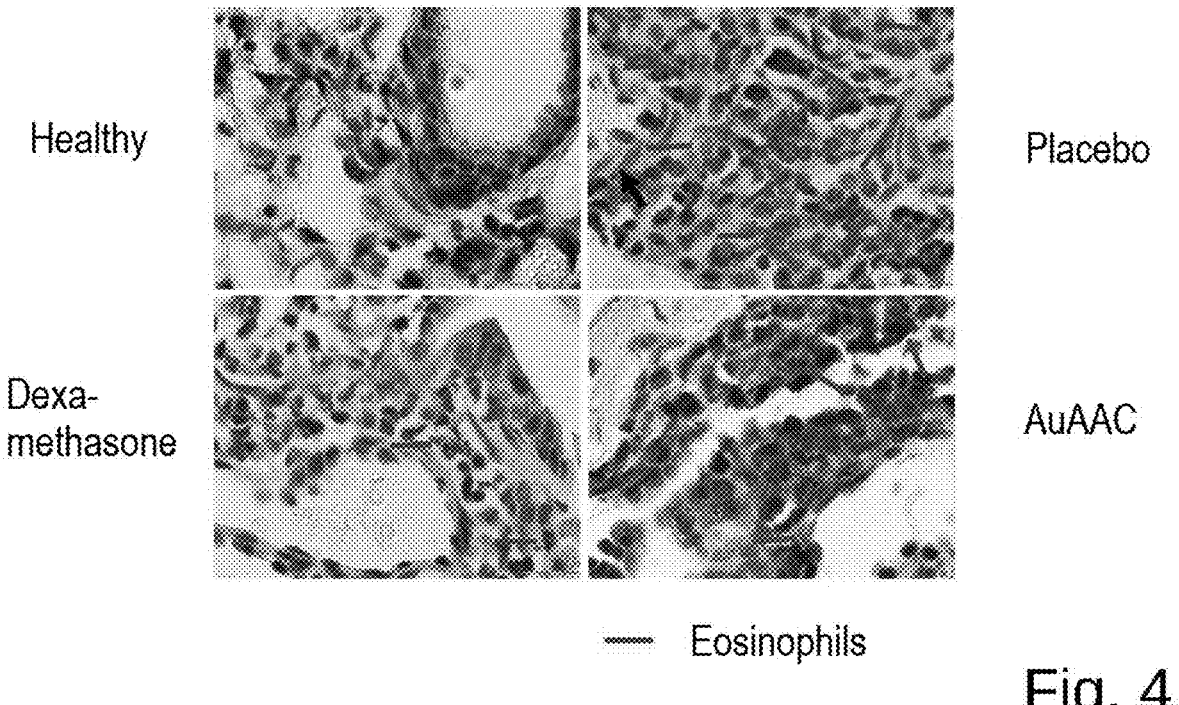
FIG. 4. Anti-inflammatory effectiveness of auroacetylcysteine in a mouse model for acute allergic asthma: investigation of lung tissue with HE and LUNA staining.
Figure 5:
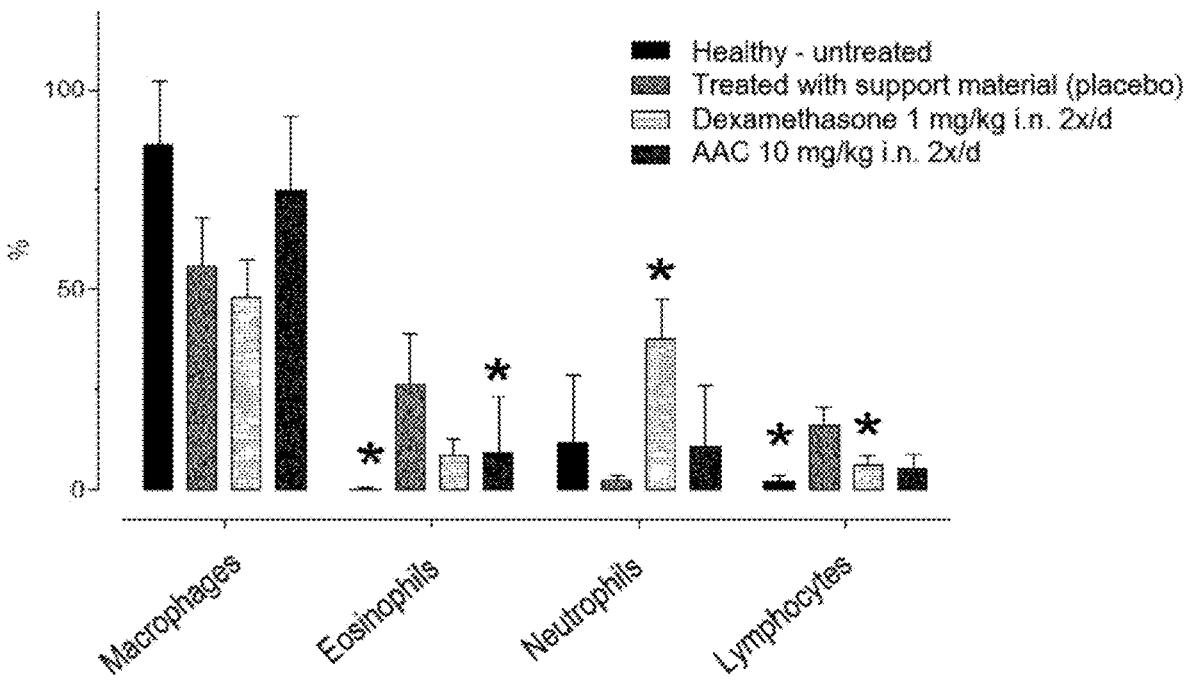
FIG. 5. Anti-inflammatory effectiveness of auroacetylcysteine in a mouse model for acute allergic asthma: investigation of cell populations. Graph: mean±SD, n=5 except for AAC group (n=4 (because of one death) * P<0.05 compared with placebo (support material), Kruskal-Wallis Test, Dunn's multiple comparison test.

Example 3. Assay of the Anti-Inflammatory Action of Inhaled Auroacetylcysteine in a Pre-Clinical Pilot Study in a Mouse Model for Acute Allergic Asthma by Means of Intranasal Application The anti-inflammatory effectiveness of auroacetylcysteine (AAC) was tested in 2 doses (10 mg/kg and 100 mg/kg) in a mouse model for acute allergic asthma with 5 mice each time, compared with dexamethasone (1 mg/kg). There were 5 mice in each of 4 groups: AAC/dexamethasone/placebo (vehicle)/untreated in triplicate per group in a setup for intranasal application in an aerosol chamber (FIG. 1). The evaluation was carried out as follows: inflammation of the respiratory tract was determined by bronchoalveolar lavage (BAL). To this end, the cell count was determined in the bronchoalveolar lavage (FIG. 2). There was a significant difference compared with the placebo. The reduction of the total cell count was comparable with dexamethasone. The inflammation of the lung tissue was determined by means of a histological investigation (FIG. 3), HE and LUNA staining (FIG. 4); mucous production was determined by means of PAS staining. Compared with dexamethasone, however, different cell populations were influenced. Primarily eosinophilic and neutrophilic granulocytes as well as lymphocytes were reduced by AAC. Macrophages were increased compared with dexamethasone. (FIG. 5). In addition, the serum-specific Ag-IgG1 was measured (ELISA). The following results were obtained: auroacetylcysteine reduced the inflammatory parameters both peribronchially as well as in the parenchyma in a concentration of 10 mg/kg. The anti-inflammatory effect in the tissue was comparable with that of dexamethasone. The treatment of mice with acute exacerbation of allergic asthma with 10 mg/kg auroacetylcysteine over 5 days reduced the total number of inflammatory cells in the bronchial secretions, the extent of the inflammation in the respiratory tract, the number of eosinophils and neutrophiles in the respiratory tract, infiltrates of inflammatory cells in the lung parenchyma.

Example 4. Production of Auroacetylcysteine 5 g of tetrachloroauric acid was mixed with 5 mL of water and cooled with ice. 3.18 g of 2,2'-thiodiethanol was added dropwise over 45 minutes, with vigorous stirring. Addition was complete when the solution was colourless and free from precipitate. 1.75 g of N-acetylcysteine in 27 mL of water was added slowly to this solution, with the formation of a white precipitate. This suspension was stirred for 1 hour and filtered through a vacuum filter. The precipitate was washed with 30 mL of water to which 1 drop of 2 N hydrochloric acid had been added, and then dried overnight. Auroacetylcysteine was obtained in a quantitative yield.

Example 5. Inhibition of SARS-CoV-2 Protease PLpro by Gold Compounds

The inhibition of the SARS-CoV-2 protease Papain-Like Protease (PLpro) was determined as follows: the test substances were dissolved in water as stock solutions and diluted one hundred-fold with HEPES buffer (50 mM HEPES, pH 7.5, 0.1 mg/mL foetal calf serum, 0.1% Triton-X-100), so that micromolar concentrations were obtained. Volumes of 50 $\mu$L of a 200 nM solution of SARS-CoV-2 PLpro in HEPES buffer or pure HEPES buffer (negative control) were pipetted into the wells of a black 96-well microtitre plate. 50 $\mu$L of the solutions of the test substances or pure HEPES buffer were added to each well (positive control) and the resulting solutions were mixed and incubated for one hour at 37° C. Next, a volume of 100 $\mu$L of a 100 $\mu$M solution of the substrate Z-Arg-Leu-Arg-Gly-Gly-AMC was added to all of the samples, mixed thoroughly, and the fluorescence emission was recorded over 10 minutes every 30 seconds ($\lambda_{ex}$=355 nm, $\lambda_{em}$=460 nm, 37° C., Victor™ X4 Perkin Elmer 2030 microplate reader). The increase in the fluorescence emission followed a linear trend ($r^2$>0.97) and the enzyme activities in the individual samples were determined as the slopes thereof. The percentage calculation of the enzyme activity was given with respect to the untreated control (positive control). The results for the negative controls were used in order to confirm the absence of false positive results, for example by reaction of the test substance with the substrate. The $IC_{50}$ values were considered to be those concentrations at which the test substance inhibited the enzyme activity by 50% compared with the positive control.

Figure 6A:
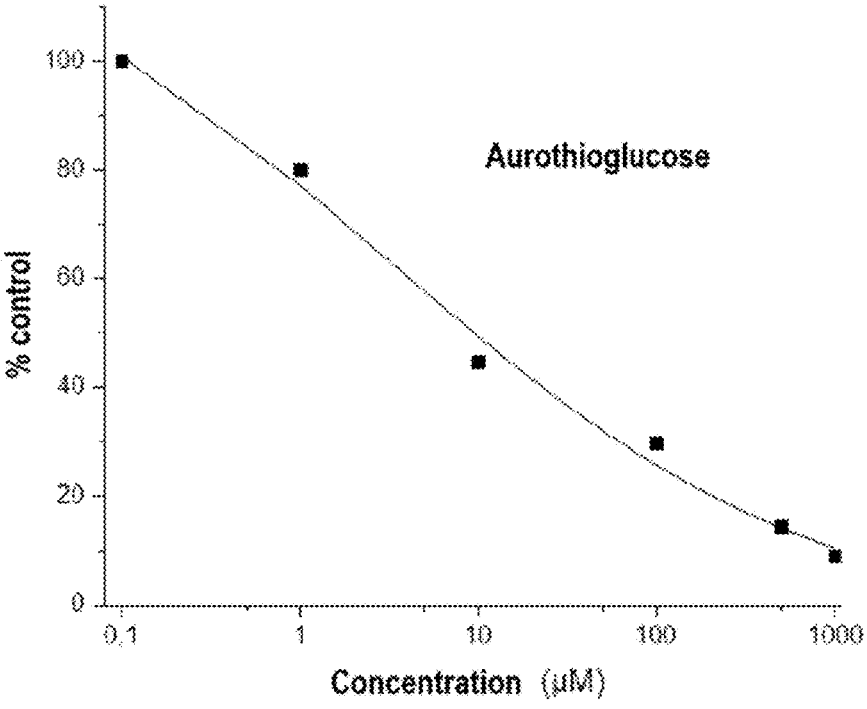
FIG. 6. Dose-effect curves for aurothioglucose (6A), aurothioglucose/N-acetylcysteine in a ratio of 1/2 (6B) and aurothiomalate (6C) as an inhibitor of SARS-CoV-2 PLpro.
Figure 6B:
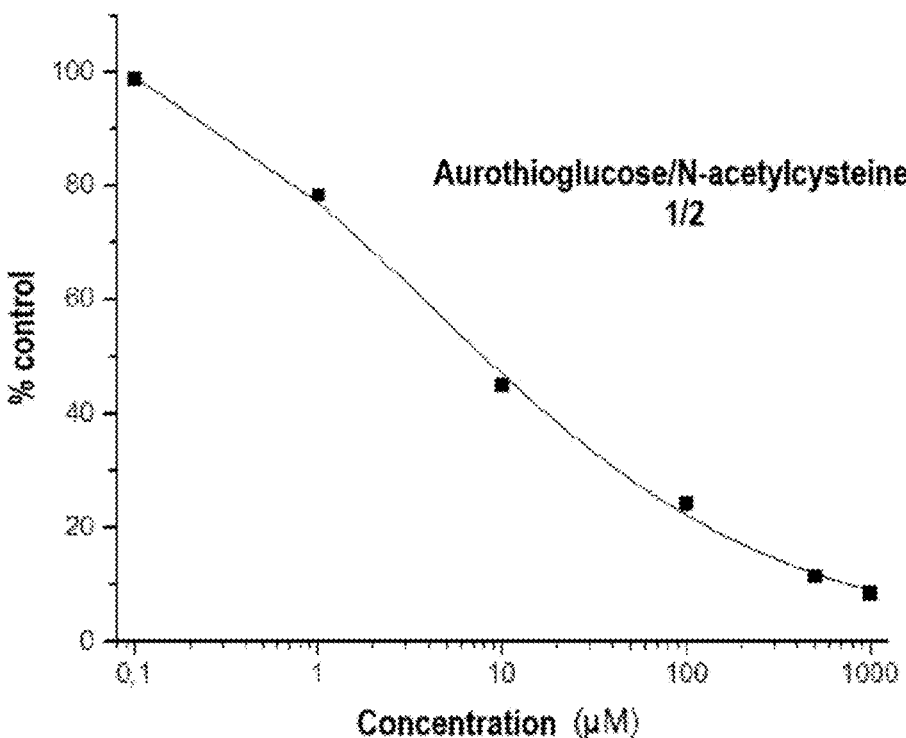
Figure 6C:
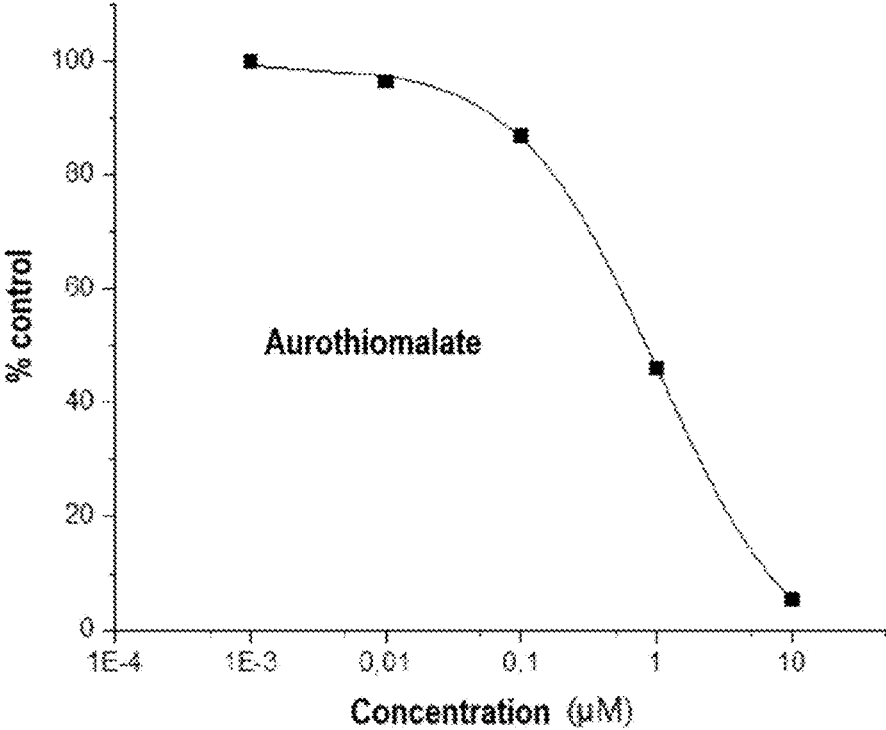

Results: the following $IC_{50}$ values were determined from the dose-effect curves (FIG. 6):

Aurothioglucose: 7.03 $\mu$M (+/−2.31 $\mu$M)

Aurothioglucose/N-acetylcysteine in a molar ratio of 1/2: 9.55 $\mu$M (+/−1.61 $\mu$M) (with respect to the quantity of aurothioglucose)

Aurothiomalate: 0.60 $\mu$M (+/−0.25 $\mu$M)

Figure 7:
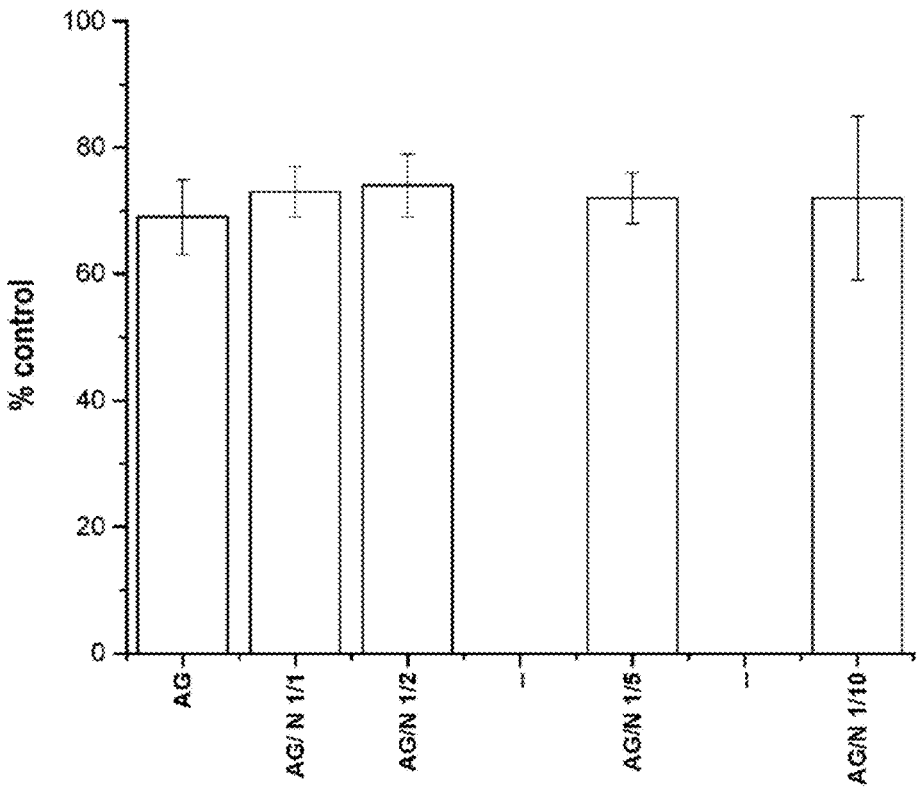
FIG. 7. Influence of added N-acetylcysteine on the inhibition of SARS-CoV-2 PLpro by 1.0 μM aurothioglucose (n=2-3). AG=aurothioglucose; N=N-acetylcysteine. The ratios given are molar ratios.

The addition of more equivalents of N-acetylcysteine to aurothioglucose did not substantially change the inhibition of the PLpro (FIG. 7).

Example 6. Inhibition of the Interaction of the SARS-CoV-2 Spike Protein with the ACE2-Receptor The influence of the test substances on the spike/ACE2 interaction can be determined by ELISA. To this end, a 96-well plate was coated with the receptor binding domains of the spike protein and stored overnight at 4° C. The wells of the microtitre plate were emptied, replaced with a blocking solution for 2 hours, washed and emptied. The test substances and controls were added to the mixture with the ACE2 receptor and incubated for one hour at 37° C. The wells were washed. Streptavidin-horseradish peroxidase conjugate was added and incubation was carried out for one hour at room temperature. After washing again, 3,3',5,5'-tetramethylbenzidine was added to a solution. After 5 minutes at room temperature, the absorption was determined at 450 nm (Perkin Elmer Victor X4 microplate reader). The activity remaining after the inhibitor addition was calculated as a percentage with respect to the untreated control.

Figure 8:
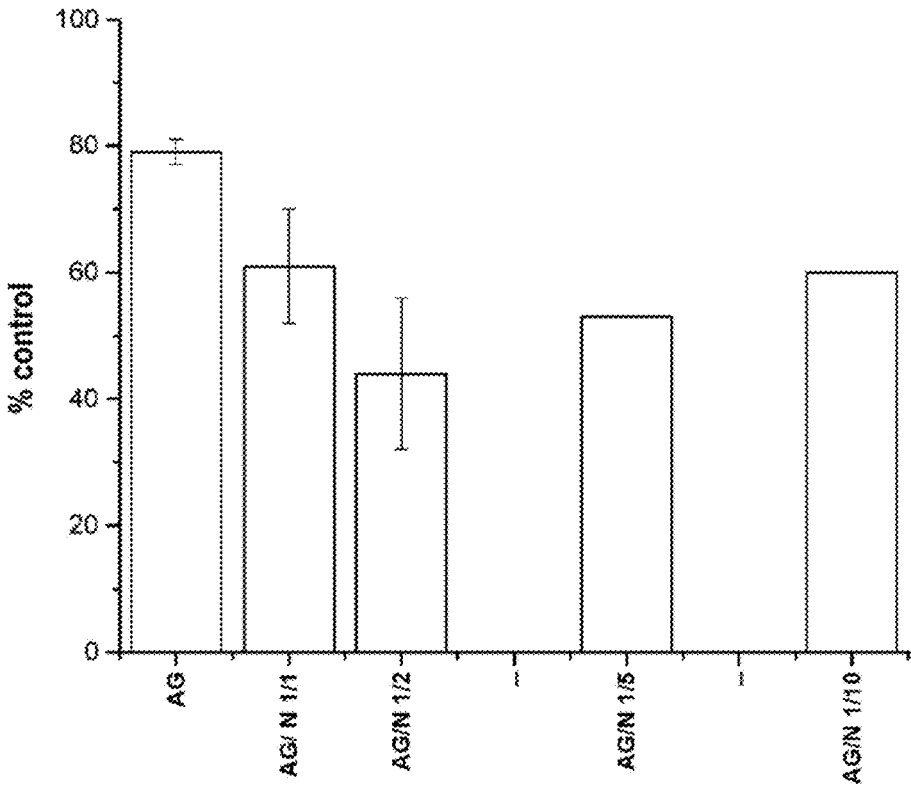
FIG. 8. Activating influence of added N-acetylcysteine on the inhibition of the spike/ACE2 interaction by 20 μM aurothioglucose. N-acetylcysteine alone produced no inhibition of the spike/ACE2 interaction (97% of control at 100 μM). AG=aurothioglucose; N=N-acetylcysteine. The ratios given are molar ratios.

Result:

20 $\mu$M aurothioglucose resulted in an inhibition of the spike/ACE2 interaction (FIG. 8). The inhibition could be substantially increased by adding N-acetylcysteine. A molar ratio of aurothioglucose to N-acetylcysteine of 1:2 proved to be particularly effective.

Example 7. Cytotoxicity in CaLu-3 Cells

In order to determine the cytotoxicity, CaLu-3 cells were cultured in 96-well microtitre plates. The cell culture medium was replaced with fresh medium which contained the gold compounds in concentrations of 25, 50 or 100 µM and incubated for 24 hours at 37° C./5% $CO_2$. Next, the remaining cells were photometrically determined using crystal violet stain (Victor X4 microplate reader). The quantity of cells in the treated samples was calculated as a percentage with respect to an untreated control.

Figure 9:
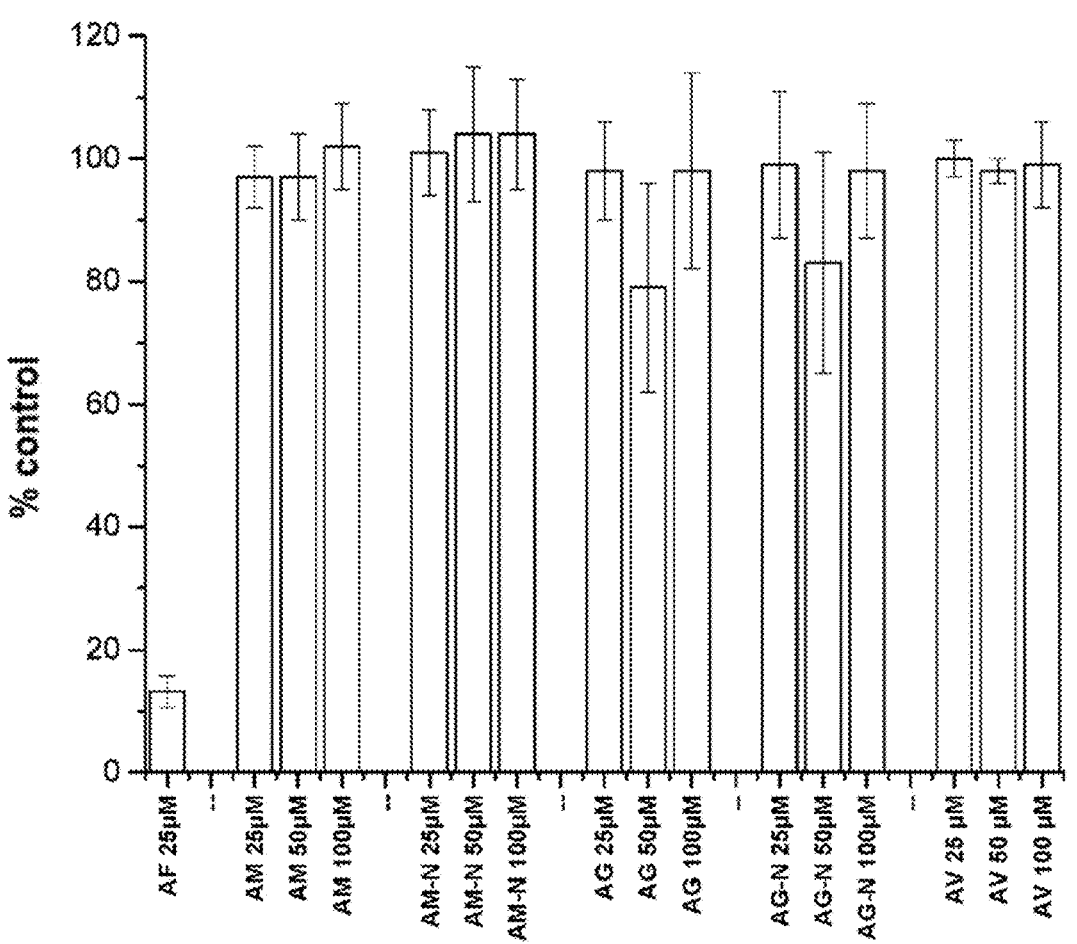
FIG. 9. Cytotoxicity of auranofin (AF), aurothiomalate (AM), aurothioglucose (AG), and the combinations of AM or AG with N-acetylcysteine (N) in a molar ratio of 1/2 (AM-N, AG-N, concentrations with respect to AM or AG), as well as auroacetylcysteine after 24 hours in CaLu-3 cells (n=3).

The results are shown in FIG. 9. In the experiment, auranofin exhibited toxicity in CaLu-3 cells (<20% of the untreated control at 25 µM). Aurothiomalate, aurothioglucose, the combinations of aurothiomalate or aurothioglucose with N-acetylcysteine in a molar ratio of 1:2, as well as auroacetylcysteine exhibited no relevant cytotoxicity in concentrations of up to 100 µM.

Example 8. Removal of Zinc from PLpro

In addition to a cysteine in the catalytic centre of the enzyme, the protease Plpro contains further cysteines in a zinc binding domain which stabilise the structure and function of the enzyme. The removal of the bound zinc constitutes an interesting mechanism for the action of inhibitors for PLpro.

In order to establish whether the inhibitors are Zn-removing agents, the presence of the $Zn^{2+}$ cation in solution was determined as follows. The inhibitor compounds were prepared as stock solutions in DMSO, as stock solutions in water or DMSO and diluted one hundred-fold with HEPES buffer (50 µM HEPES, pH 7.5) to 100 µM concentrations. Volumes of 50 µL of SARSCoV-2 PLpro (Elabscience) in HEPES buffer or blank HEPES buffer (control for false positive results) were placed in the wells of a black 96-well microtitre plate (Nunclon, Nunc). Volumes of 50 µL of the inhibitor solutions or 1% DMSO in HEPES buffer (control) were added. The resulting solutions (500 nM SARS-CoV-2 PLpro, 0.5% DMSO, 50 µM test compound or blank HEPES buffer) were mixed. A volume of 100 µL with 2.0 µM of the zinc-specific fluorophore FluoZin™-3 (Invitrogen/LifeTechnologies) was added to all of the wells. The resulting solutions were mixed and the fluorescence emission was determined after 10 min, every 10 min over a period of 90 minutes, at 37° C. ($\lambda_{exc}$=485 nm, $\lambda_{em}$=535 nm); Victor X4 microtitre plate reader). The relative fluorescence was calculated by dividing the absolute fluorescence emission of the well which contained the inhibitor by the absolute fluorescence of the corresponding well which contained the enzyme but no inhibitor (control). Wells which contained the inhibitor but no enzyme were used to check for false positive results. None of the tested compounds exhibited false positive results.

Figure 10:
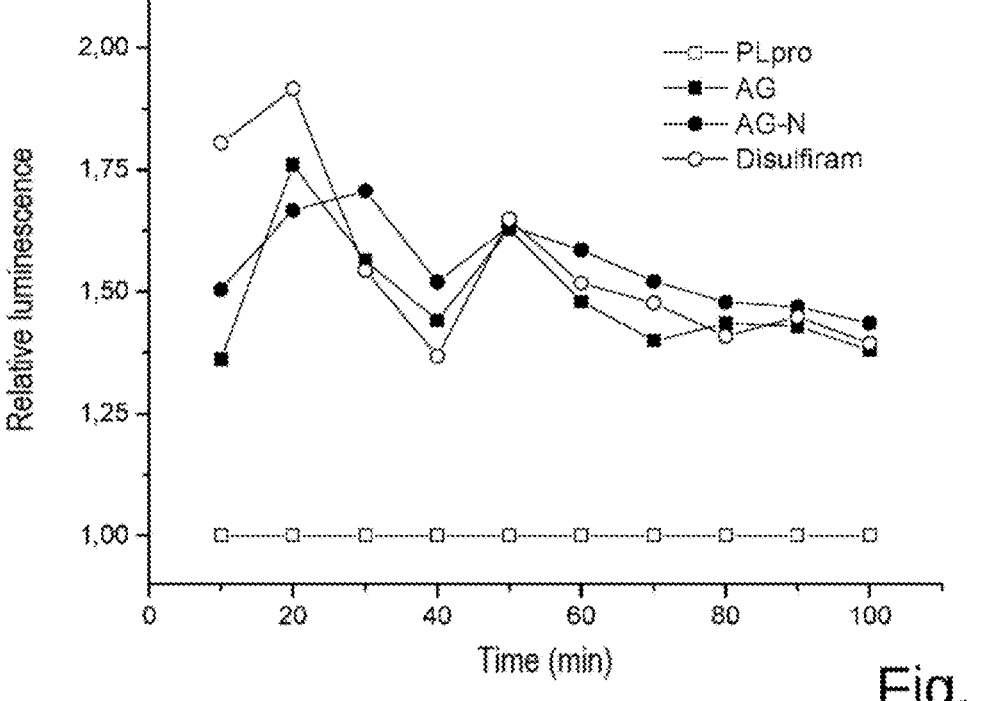
FIG. 10. Removal of zinc from PLpro by disulfiram, aurothioglucose (AG) and the mixture of aurothioglucose with N-acetylcysteine in a molar ratio of 1:2 (AG-N). (values given in comparison with untreated enzyme (PLpro)).

As can be seen in FIG. 10, aurothioglucose as well as the mixture of aurothioglucose with acetylcysteine resulted in removal of zinc from the PLpro which was comparable with the reference compound disulfiram. These results are in agreement with the inhibition of the enzyme activity of PLpro by aurothioglucose and are further confirmation of its relevance.

Example 9. Inhibition of the SARS-CoV-2 Protease 3CLpro by Gold Compounds

The inhibition of the SARS-CoV-2 protease 3CLpro was determined as follows: the test substances were dissolved in water as stock solutions and diluted one hundred-fold with HEPES buffer (50 mM HEPES, pH 7.5, 0.1 mg/mL foetal calf serum, 0.1% Triton-X-100), so that micromolar concentrations were obtained. Volumes of 50 µL of a 300 nM solution of SARS-CoV-2 3CL protease (Mpro) MBP-tag in HEPES buffer or pure HEPES buffer (negative control) were pipetted into the wells of a black 96-well microtitre plate. 50 µL of the test substance solutions or pure HEPES buffer (positive control) was respectively added thereto and the resulting solutions were mixed and incubated for one hour at 37° C. Next, a volume of 100 µL of a 50 µM solution of the substrate DABCYL-Lys-Thr-Ser-Ala-Val-Leu-Gln-Ser-Gly-Phe-Arg-Lys-Met-Glu-EDANS trifluoroacetate was added to all of the samples, mixed thoroughly, and the fluorescence emission was recorded every 3 minutes over 75 minutes ($\lambda_{ex}$=60 nm, $\lambda_{em}$=460 nm, 37° C., Victor™ X4 Perkin Elmer 2030 microtitre plate reader). The evaluation was carried out in an analogous manner to the method with PLpro.

Results: the gold compounds are good inhibitors for SARS-CoV-2 3CLpro. The following $IC_{50}$ values were determined: auranofin: 11.69 µM (±0.40 µM); aurothioglucose: 8.25 µM (±0.04 µM); aurothiomalate: 22.89 µM (±0.72 µM).

Example 10. Inhibition of Infectivity of Bovine Coronavirus (BCoV) in Cell Structure As a surrogate for SARS-CoV-2, upon which experiments can only be carried out in biosafety level 3 (BSL3) laboratories, bovine coronavirus (BCoV), a virus which is related to SARS-CoV-2, which is also classified in the Betacoronavirus genus, was used because these experiments could be carried out in the lower biosafety level 2, BSL2. The receiving cell cultures used were Madin Darby Bovine Kidney (MDBK) cells.

After incubating different concentrations of aurothioglucose with 100 Tissue Culture Infectious Dose 50 (TCID50) of bovine coronavirus at 37° C. for one hour, the aurothioglucose-bovine coronavirus suspension was inoculated onto the MDBK cells receiving this virus and incubation was carried out for a further 12-48 hours at 37° C. and under a 5% $CO_2$ atmosphere. At an aurothioglucose concentration of 256 µM, a 10-fold reduction in the viral load was observed.

Adding 64 µM favipiravir at the time of inoculating the aurothioglucose-bovine coronavirus suspension onto the cell cultures also resulted in a reduction in the viral load formed.

Example 11. Therapeutic Treatment

In order to prepare a preparation A, 3 mg of micronized aurothioglucose are blended with 9 mg of lactose and placed in a multi-dose powder inhaler. Four Covid-19 patients with the onset of symptoms less than 48 hours prior to the start of treatment are treated by administration of 2 spray applications each of 200 µg of the powder formulation over a period of 10 days, 2×daily.

In order to prepare a combination preparation B, liquid ampoules are produced, each with 0.1 mg of aurothioglucose and 0.4 mg of N-acetylcysteine dissolved in 2.5 mL of water. Four artificially ventilated Covid-19 patients are treated with one liquid ampoule per day by means of a nebulizer over a period of 10 days.

REFERENCES

Ahmed Abdel Khaleka, Nader S. Abutaleba, Haroon Mohammada, and Mohamed N. Seleema: Antibacterial and antivirulence activities of auranofin against *Clostridium difficile*. Int J Antimicrob Agents. 2019 January; 53(1): 54-62. doi:10.1016/j.ijantimi-cag.2018.09.018

Manish Bodas and Neeraj Vij; The NFkB Signaling in Cystic Fibrosis Lung Disease: Pathophysiology and Therapeutic Potential. Discov. Med. 2010 April; 9(47); 346-356

Rene Broer, Bertrand Boson, Willy Spaan, Francois-Loic Cosset, and Jeroen Corver; Important Role for the Transmembrane Domain of Severe Acute Respiratory Syndrome Coronavirus Spike Protein during Entry. J. Virol., February 2006, p. 1302-1310 Vol. 80, No. 3 0022-538X/06/$08 0.000 doi:10.1128/JVI.80.3.1302-1310.2006

Kevin W. Chang, Yi Wei Sheng, and James L. Gombold, Coronavirus-Induced Membrane Fusion Requires the Cysteine-Rich Domain in the Spike Protein. Virology 269, 212-224 (2000) doi:10.1006/viro.2000.0219

Ahmed Elkashif and Mohamed N. Seleem, Investigation of auranofin and gold-containing analogues antibacterial activity against multidrug-resistant *Neisseria gonorrhoeae*. Sei. Rep. 2020 March; 10; 5602

Maria Gil-Moles, Uttara Basu, Rolf Büssing, Henrik Hoffmeister, Sebastian TUrck, Agnieszka Varchmin, Ingo Ott, Gold Metallodrugs to Target Coronavirus Proteins: Inhibitory Effects on the Spike-ACE2 Interaction and on PLpro Protease Activity by Auranofin and Gold Organometallics. Chem. Eur. J. 2020 September; https://doi.org/10.1002/chem. 202004112

Rodriguez-Izquierdo I, Serramia M J, Gomez R, De La Mata F J, Bullido M J, and Munoz-Fernández M A, Gold Nanoparticles Crossing Blood-Brain Barrier Prevent HSV-1 Infection and Reduce Herpes-Associated Amyloid-ß secretion. J. Clin. Med. 2020, 9, 155; doi:10.3390/jcm9010155

The invention claimed is:

1. A medicament for inhalation, containing
aurothioglucose; and
N-acetylcysteine;
    wherein the medicament contains aurothioglucose and N-acetylcysteine in a molar ratio of between 1:10 and 1:1 (aurothioglucose: N-acetylcysteine).

2. The medicament for inhalation as claimed in claim 1, further containing a virostatic.

3. The medicament as claimed in claim 1, wherein the medicament contains aurothioglucose and N-acetylcysteine in a molar ratio of between 1:5 and 1:1 (aurothioglucose: N-acetylcysteine).

4. The medicament for inhalation as claimed in claim 1, further containing
    an active substance selected from hydroxychloroquine, chloroquine and ivermectin.

5. The medicament as claimed claim 1, wherein the medicament further contains a support material comprising a carbohydrate.

6. The medicament as claimed in claim 1, wherein the medicament is presented as a powder formulation.

7. The medicament as claimed in claim 1, wherein the medicament is presented as a solution.

8. An inhaler containing a medicament as claimed in claim 1.

9. A method for treating an infectious or mixed inflammatory and infectious lung disease in a subject in need thereof, comprising administering to the subject a therapeutically effective amount of the medicament according to claim 1.

10. The method as claimed in claim 9, wherein the lung disease is a lung infection.

11. The method as claimed in claim 9, wherein the lung disease is a disease which is caused by Coronaviridae.

12. The method as claimed in claim 9, wherein the medicament is administered in a dose containing the aurothioglucose in an amount to provide between 0.001 μmol and 450 μmol of gold.

13. The method as claimed in claim 9, wherein the medicament is administered in a dose containing the aurothioglucose in an amount to provide between 0.1 μg and 1000 μg of gold per kg of body weight of the patient.

14. The method as claimed in claim 9, wherein the medicament is administered to the subject by means of inhalation.

15. The method as claimed in claim 9, wherein the medicament is administered to the subject by means of an inhaler.

16. The method as claimed in claim 9, wherein the lung disease is a viral or mixed viral and bacterial lung infection.

17. The method as claimed in claim 9, wherein the lung disease is a disease which is cased by SARS-COV-1, SARS-COV-2 or MERS-COV.

18. The method as claimed in claim 9, wherein the medicament is administered to the subject by means of liquid inhalation or powder inhalation.

19. The method as claimed in claim 9, wherein the medicament is administered to the subject by means of a powder inhaler, dosing inhaler or nebulizer.

20. The medicament as in claim 3, wherein the medicament contains aurothioglucose and N-acetylcysteine in a molar ratio of between 1:2.5 and 1:1.5 (aurothioglucose: N-acetylcysteine).

21. The medicament as in claim 20, wherein the medicament contains aurothioglucose and N-acetylcysteine in a molar ratio of 1:2 (aurothioglucose: N-acetylcysteine).

\* \* \* \* \*